United States Patent
Shaevitz et al.

(10) Patent No.: US 11,803,974 B2
(45) Date of Patent: Oct. 31, 2023

(54) AUTOMATED SYSTEM TO MEASURE MULTI-ANIMAL BODY PART DYNAMICS

(71) Applicant: The Trustees of Princeton University, Princeton, NJ (US)

(72) Inventors: Joshua W. Shaevitz, Princeton, NJ (US); Mala Murthy, Princeton, NJ (US); Talmo D. Pereira, Princeton, NJ (US); Diego E. Aldarondo, Somerville, MA (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 282 days.

(21) Appl. No.: 17/282,818

(22) PCT Filed: Oct. 4, 2019

(86) PCT No.: PCT/US2019/054723
§ 371 (c)(1),
(2) Date: Apr. 5, 2021

(87) PCT Pub. No.: WO2020/072918
PCT Pub. Date: Apr. 9, 2020

(65) Prior Publication Data
US 2021/0357630 A1    Nov. 18, 2021

Related U.S. Application Data

(60) Provisional application No. 62/741,643, filed on Oct. 5, 2018, provisional application No. 62/829,318, filed on Apr. 4, 2019.

(51) Int. Cl.
*G06T 7/246*    (2017.01)
*G06F 3/04845*    (2022.01)
(Continued)

(52) U.S. Cl.
CPC .......... *G06T 7/246* (2017.01); *G06F 3/04845* (2013.01); *G06F 18/23213* (2023.01);
(Continued)

(58) Field of Classification Search
CPC ................ G06T 7/246; G06T 7/251; G06T 2207/10016; G06T 2207/20101;
(Continued)

(56) References Cited

U.S. PATENT DOCUMENTS 6,311,644 B1    11/2001    Pugh
10,121,064 B2 *    11/2018    Hong ................ A61B 5/7267
(Continued)

OTHER PUBLICATIONS

Rodriguez, I. F., et al., "Multiple Insect and Animal Tracking in Video using Part Affinity Fields", Workshop Visual observation and analysis of Vertebrate And Insect Behavior (VAIB) at International Conference on Pattern Recognition (ICPR), Aug. 2018.*
(Continued)

*Primary Examiner* — Xuemei G Chen
(74) *Attorney, Agent, or Firm* — MEAGHER EMANUEL LAKS GOLDBERG & LIAO, LLP (57) ABSTRACT

Disclosed are a system and method for quantifying changes in animal posture from video recordings of multiple interacting animals. Also disclosed are a system and method for training a posture identification algorithm efficiently with minimal human effort and evaluating the posture of millions of animal images. The disclosed process employs video recordings of behaving animals to produce a full set of geometrical coordinates for each body part over time. Inter alia, the disclosed system should be useful for organizations interested in doing large small-molecule screens to find drugs that affect the behavior of animals, and for those investigating new behavioral diagnostics for human patients. The disclosed system allows one to record video of animals and then automatically calculate the position of each body
(Continued)

part over time. The output of this calculation can be used for simple analysis of the amount of movement for specific body parts, or part of a more complex scheme for measuring behaviors.

21 Claims, 4 Drawing Sheets

(51) Int. Cl.
| | |
|---|---|
| *G06N 3/04* | (2023.01) |
| *G06N 3/08* | (2023.01) |
| *G06V 40/10* | (2022.01) |
| *G06V 20/40* | (2022.01) |
| *G06F 18/23213* | (2023.01) |
| *G06V 10/764* | (2022.01) |
| *G06V 10/82* | (2022.01) |
| *G06V 10/50* | (2022.01) |
| *G06V 40/20* | (2022.01) |

(52) U.S. Cl.
CPC ............ *G06N 3/04* (2013.01); *G06N 3/08* (2013.01); *G06T 7/251* (2017.01); *G06V 10/50* (2022.01); *G06V 10/764* (2022.01); *G06V 10/82* (2022.01); *G06V 20/46* (2022.01); *G06V 40/10* (2022.01); *G06V 40/20* (2022.01); *G06T 2207/10016* (2013.01); *G06T 2207/20101* (2013.01)

(58) Field of Classification Search
CPC . G06T 2207/20081; G06T 2207/20092; G06T 2200/24; G06T 2207/20084; G06F 3/04845; G06F 18/23213; G06N 3/04; G06N 3/08; G06V 10/50; G06V 10/764; G06V 10/82; G06V 20/46; G06V 40/10; G06V 40/20; A61B 5/1114; A61B 5/1127; A61B 5/16; A61B 5/7267; A61B 2503/40
See application file for complete search history.

(56) References Cited

U.S. PATENT DOCUMENTS

| | | | |
|---|---|---|---|
| 11,134,221 B1* | 9/2021 | Brown | H04N 5/2621 |
| 2004/0131254 A1 | 8/2004 | Liang et al. | |
| 2006/0110049 A1 | 5/2006 | Liang et al. | |
| 2010/0086215 A1* | 4/2010 | Bartlett | G06V 40/176 |
| | | | 382/224 |
| 2012/0172700 A1* | 7/2012 | Krishnan | A61B 6/505 |
| | | | 600/407 |
| 2015/0309581 A1* | 10/2015 | Minnen | G06T 7/194 |
| | | | 382/103 |
| 2015/0327518 A1* | 11/2015 | Han | A61D 17/00 |
| | | | 348/143 |
| 2016/0196665 A1* | 7/2016 | Abreu | G06T 11/00 |
| | | | 345/427 |
| 2016/0262355 A1 | 9/2016 | Swan | |
| 2017/0208445 A1* | 7/2017 | Tuan | G08B 21/10 |
| 2017/0251985 A1* | 9/2017 | Howard | G16H 70/60 |
| 2017/0278266 A1* | 9/2017 | Hassan | G06T 7/248 |
| 2018/0024641 A1* | 1/2018 | Mao | A63F 13/428 |
| | | | 382/103 |
| 2018/0047137 A1* | 2/2018 | Angara | G06V 40/171 |
| 2018/0092573 A1 | 4/2018 | Datta et al. | |
| 2018/0365532 A1* | 12/2018 | Molchanov | G06N 3/084 |
| 2019/0014884 A1* | 1/2019 | Fu | G06V 20/20 |
| 2019/0087965 A1* | 3/2019 | Datta | G06T 7/215 |
| 2019/0325203 A1* | 10/2019 | Yao | G06V 10/82 |
| 2020/0337272 A1* | 10/2020 | Kumar | A01K 1/031 |

OTHER PUBLICATIONS

International Search Report and Written Opinion for corresponding PCT Application No. PCT/US2019/054723, dated Jan. 2, 2020.

* cited by examiner

AUTOMATED SYSTEM TO MEASURE MULTI-ANIMAL BODY PART DYNAMICS

CROSS-REFERENCE TO RELATED APPLICATIONS

This application claims priority to U.S. Provisional Application No. 62/741,643, filed Oct. 5, 2018, and U.S. Provisional Application No. 62/829,318, filed Apr. 4, 2019, both of which are herein incorporated by reference in their entirety.

STATEMENT REGARDING FEDERALLY SPONSORED RESEARCH OR DEVELOPMENT

This invention was made with government support under Grant No. NS104899 awarded by the National Institutes of Health and support under Grant No. 1451197 awarded by National Science Foundation. The government has certain rights in the invention.

FIELD OF THE INVENTION

The present invention relates to monitoring animal behavior, and specifically to deep-learning methods for predicting the positions of animal body parts.

BACKGROUND

Connecting neural activity with behavior requires methods to parse what an animal does into its constituent components (e.g., movements of its body parts), which can then be connected with the electrical activity that generates each action. This is particularly challenging for natural behavior, which is dynamic, complex, and seemingly noisy. Human classification of behavior is slow and subject to bias, but speed can be increased through automation including methods to track and analyze animal centroids and shapes over time, machine learning techniques for identifying user-defined behaviors, such as fighting or courting, and software to segment the acoustic signals produced by an animal. However, one may not know a priori which behaviors to analyze—this is particularly true when screening mutant animals or investigating the results of neural perturbations that can alter behavior in unexpected ways.

Traditionally, approaches for monitoring animal behavior involve hand annotation of body movements, which is intractable for any large analysis (including large screens, studying moving body kinematics for engineering purposes, or animal detection and monitoring for agro-business, or for wildlife), cannot be automated, and prevents the detection of subtle changes in movement which can only be seen through quantitative statistical analyses.

Recent developments in the unsupervised clustering of postural dynamics have overcome many of these challenges by analyzing the raw frames of movies in a reduced dimensional space (e.g., generated using Principal Component Analysis (PCA)). By comparing frequency spectra or fitting auto-regressive models from low-dimensional projections, these methods can both define and record the occurrence of tens to hundreds of unique, stereotyped behaviors in animals such as fruit flies or mice. Such methods have been used to uncover new structure in behavioral data, facilitating the investigation of temporal sequences, social interactions, the analysis of genetic mutants, and the results of neural perturbation.

A major drawback to the aforementioned techniques is their reliance on PCA to reduce the dimensionality of the image time series. While this produces a more manageable substrate for machine learning, it would be advantageous to directly analyze the position of each actuatable body part as this is what is ultimately under the control of the motor nervous system. However, measuring all of the body part positions from raw images is a challenging computer vision problem. Previous attempts at automated body-part tracking in insects and mammals have relied on either physically constraining the animal and having it walk on a spherical treadmill or linear track, applying physical markers to the animal, or utilizing specialized equipment such as depth cameras, frustrated total internal reflection imaging or multiple cameras. However, these techniques are all designed to work within a narrow range of experimental conditions and are not easy to adapt to disparate datasets.

Thus, a technique that can work in a wide range of conditions and can be readily adapted to disparate datasets is needed and useful for, e.g., scientific experiments.

BRIEF SUMMARY

Disclosed an automated system for measuring and predicting animal body part dynamics. The system utilizes a processor and memory containing machine readable instructions that, when executed, utilize a variety of steps, including: (1) displaying one or more graphical user interfaces that allows a user to select at least one video recording of one or more animals behaving; (2) generating a set of suggested frames for labeling by extracting image features from random frames within the videos, grouping them according to similarity, selecting a similarly sized subset from each group, meant to promote diversity in suggestions; (3) displaying one or more graphical user interfaces that (a) allows the user to navigate to and view individual frames within the selected video, (b) allows the user to specify a skeleton of at least one of the one or more animals to be tracked, (c) allows the user to label video frames by creating instances of the skeleton on top of the image and then positioning each landmark of each instance at their correct location within the images via draggable markers, and (d) allows the user to select between pre-configured profiles for training neural network modules based on the labeled data; (3) optionally trains a region proposal module for detecting the center or extent of a region that the animal(s) occupy within an image; (4) trains a landmark detection module for detecting landmarks resembling the ones labeled by the user in appearance and context to; (5) optionally trains a landmark grouping module for grouping detected landmarks based on the connections specified in the skeleton; (6) optionally executes or trains a tracking module for grouping detections of the same animals across frames; (7) executes a region proposal module, landmark detection module, landmark group module, and tracking module to predict the extent of animals, locations of body landmarks, and connections between detected body landmarks, on any new images of the same animals or those that resembling in appearance and context; (8) predicting and optionally groups body part landmarks of animals within the unlabeled suggested images; (9) displaying a graphical user interface for inspection and correction of the results for further training, optionally prioritized by prediction score; (10) executing all modules configured or trained by the user on any new videos of the same or similar animals; and (11) displaying a graphical user interface for inspection and proofreading of the results.

Optionally, the video recordings of animals behaving comprise sequential images of the same animals or those of any species resembling in appearance and context, collected under the same imaging conditions or those resembling in lighting, color, distance and orientation to the animals.

The skeleton to be tracked comprises a set of named nodes representing identifiable landmarks on the body of the animal, and a set of ordered pairs of named nodes representing the connections between the nodes.

Optionally, generating suggested frames for labeling comprises a set of machine readable instructions for randomly sampling frames from the selected videos, summarizing the contents of these images, applying the k-means clustering algorithm to these summary descriptions, and then sampling a fixed maximum number of images from each cluster, wherein summarization of images includes: (a) flattening all image pixels, computing their principal components via eigen decomposition, and projecting each image onto a user-specified number of top principal components as defined by their variance explained; (b) detecting interest points using the Binary Robust Invariant Scalable Keypoints (BRISK) algorithm and computing the Histogram of Oriented Gradients (HOG) descriptors of the image region around each interest point; (c) detecting interest points using the BRISK algorithm and computing the BRISK descriptors of the image region around each interest point; or (d) detecting and summarizing interest points using any of the above methods, and computing the principal components of the set of image region descriptors.

Optionally, the training profiles comprise a set of configuration options that define the module type, neural network backbone type, neural network architectural parameters, data preprocessing procedure, optimization procedure, data augmentation procedure, and any other configuration options pertaining to training the core modules of the system.

Optionally, the region proposal module comprises a configurable convolutional neural network and the training and inference procedures for predicting the center or extent that animal(s) occupy within images.

Optionally, the landmark detection module comprises a configurable neural network and the training and inference procedures for predicting image coordinates of any number of instances of each landmark type.

Optionally, neural networks in the landmark detection module are trained to predict, from unmarked images of the animal, for each landmark type, a representation of the location of body landmarks (also referred to as "confidence maps") where each pixel corresponds to the probability of the body landmark being present at a given location.

Optionally, an inference procedure for neural networks in the region proposal and landmark detection modules comprises a set of machine readable instructions to find local maxima in each confidence map image, and refine these local maxima (also referred to as "peaks") by upsampling a small area around each local maxima using bicubic interpolation and finding the global maximum within these confines whose relative location is used to offset the original coordinates of each peak.

Optionally, an inference procedure for the region proposal module comprises a set of machine-readable instructions for proposing bounding boxes of fixed size around the detected centers, where the fixed size is calculated from sizes present in the labeled data or specified by the user and merged when they significantly overlap.

Optionally, the landmark grouping module comprises a configurable neural network and the training and inference procedures for predicting the connections between detected landmarks.

Optionally, the system according to claim 1, wherein neural networks in the landmark grouping module are trained to predict, from unmarked images of the animal, for each connection between landmark types, a representation of the relative spatial offset between the two body part landmarks that form the connection (also referred to as "part affinity fields") where each pixel corresponds to the unit vector that is oriented from the source landmark to the destination landmark.

Optionally, an inference procedure for neural networks in the landmark grouping module comprises a set of machine readable instructions to group pairs of landmark types optimally by evaluating the similarity of the orientation derived from the line formed by the pair of landmarks, and the orientation derived by taking the average of the unit vectors along the same line on the predicted part affinity fields.

Optionally, the tracking module comprises a set of machine-readable instructions to perform optimal matching between detected instances in different frames, by using image features as similarity or pairwise affinities learned through a configurable neural network and the training and inference procedures to produce them.

Optionally, the optimal matching in the "tracking" module utilizes a set of machine readable instructions to associate detected instances across consecutive frames by greedy assignment of maximum similarity of instances based on underlying image features or learned affinities, or by applying predicted displacements of each landmark derived from optical flow calculation and then using the similarity of the resulting body configuration to rank assignments.

Optionally, when the system comprises a configurable neural network, the configurable neural network is a layered network architecture consisting of: (a) a configurable backbone (early neural network layers) that can be any compatible convolutional neural network architecture; and (b) a configurable head (final output neural network layers) that can be any compatible neural network layers whose output resembles the output of the specific module.

Optionally, when the system comprises a backbone, the backbone comprises an architecture selected from the group consisting of LEAP CNN, UNet, Stacked Hourglass, DenseNet, ResNEt, HRNet, or a user-specified convolutional neural network architecture.

Optionally, when the system comprises a backbone, the configuration options of a backbone comprise the set of parameters that specify the variant of the backbone architecture to use, including (a) number of convolutional filters; (b) size of convolutional filters; (c) layers per block; (d) number of blocks with pooling (image feature scale reduction); (e) number of blocks with upsampling (image feature scale increase); (f) number of stacks (copies of the backbone); and (g) any parameter specific to a given backbone.

Optionally, the system specifies the: (a) data preprocessing procedure, such as image resizing or cropping to the extent of the labeled instances; (b) data augmentation procedure, such as the range of random rotations or scaling of images and corresponding labels; (c) optimizer algorithm, such as Adam or RMSprop; (d) learning rate schedule, such as the initial learning rate and how to reduce it when an optimization plateau is reached; (e) checkpointing procedure, such as how often and where to save the trained neural network; and (f) duration of the training procedure, such as the number of images per batch, the number of training batches per epoch, the number of validation batches per epoch (for detection of learning rate plateau or checkpointing), the number of epochs, and the number of epochs without improvement before early termination of training.

Optionally, the system comprises a set of machine readable instructions to execute the functionality provided by each module in a specified sequence, including: (a) executing the landmark detection module to detect peaks in full sized images without grouping; (b) executing the region proposal module to crop the image around each animal; (c) executing the landmark detection module to detect peaks in cropped images without grouping; (d) executing the landmark detection module to detect peaks in full sized images, then executing the landmark grouping module to group the detected peaks in the full sized images; (e) executing the region proposal module to crop the image around each animal, executing the landmark detection module to detect peaks in cropped images, then executing the landmark grouping module to group the detected peaks in the cropped images. Optionally, the system may execute any of (a)-(e) to detect peaks and optionally group them into instances, then executing the tracking module to group them over consecutive frames.

DETAILED DESCRIPTION

Disclosed is an automated system to measure the body part dynamics of one or more animals, including one or more classes of animals. The technique can be used with animals within many classes, including but not limited to insecta, arachnida, aves, and mammalia. For example, this system has been used for measuring body part dynamics of fruit flies, bees, mice, and giraffes. More particularly, disclosed is a process to use video recordings of behaving animals to produce a full set of geometrical coordinates for each body part over time. Further, the system can be configured to include grouping position detections (skeletons that link together individual labeled body parts) and linking them over time. Inter alia, the disclosed system should be useful for organizations interested in doing large small-molecule screens to find drugs that affect the behavior of animals, and for those investigating new behavioral diagnostics for human patients.

The disclosed system allows one to automatically calculate the position of each body part over time (hands, arms, legs, fingers, toes, head, nose, tail, etc.) in a recorded video of animals. The output of this calculation can be used for simple analysis of the amount of movement for specific body parts, or part of a more complex scheme for measuring behaviors.

The system detects the positions of individual body parts by training neural networks to infer a "confidence map" for each body part given an image of the animals. The system can convert this map of probabilities to coordinates of each detection within the image. Detections are enumerated by finding peaks for each confidence map for each body part, resulting in zero or more detections per body part per animal within the image. The system is modular with regard to the neural network architecture that generates the confidence maps.

The system can operate efficiently on large (high resolution) images where the animals may occupy a small fraction of the image through a region proposal module. The system identifies/proposes regions where animals are present by training neural networks to predict the centroid of the animals at an automatically determined fixed scale, or by training neural networks to predict the bounding box that contains each animal. The system automatically infers centroids or bounding boxes from the user labels of the full skeleton. The system is modular with regard to the neural network architecture that generates the region proposals.

The system is capable of implementing all neural network-based modules in a fashion agnostic to the "backbone" or architecture of the neural network. The system implements a gallery of previously described convolutional neural network backbones (LEAP CNN, UNet, Stacked Hourglass, DenseNet, ResNet, HRNet) and can be easily extended to include new architectures capable of producing the expected output of each module from image inputs. The system is capable of using pre-trained neural network backbones or training them from randomly initialized weights.

The system can train all modules in a pipeline that is configurable via "profiles". The system is equipped with common profiles that were empirically determined to be generally high performing on most types of data. The system executes the training procedure for any module in sequence, parallel or remotely through configuration specified in the profile. Trained modules can be executed in any combination, or independently.

After being trained one or more times, the system can generate new predictions that the user can inspect and correct through the software interface. The system uses corrected predictions in addition to entirely manually annotated images to re-train specified neural networks underlying the aforementioned modules. The system improves its accuracy through repeated iterations of this procedure.

Figure 1:
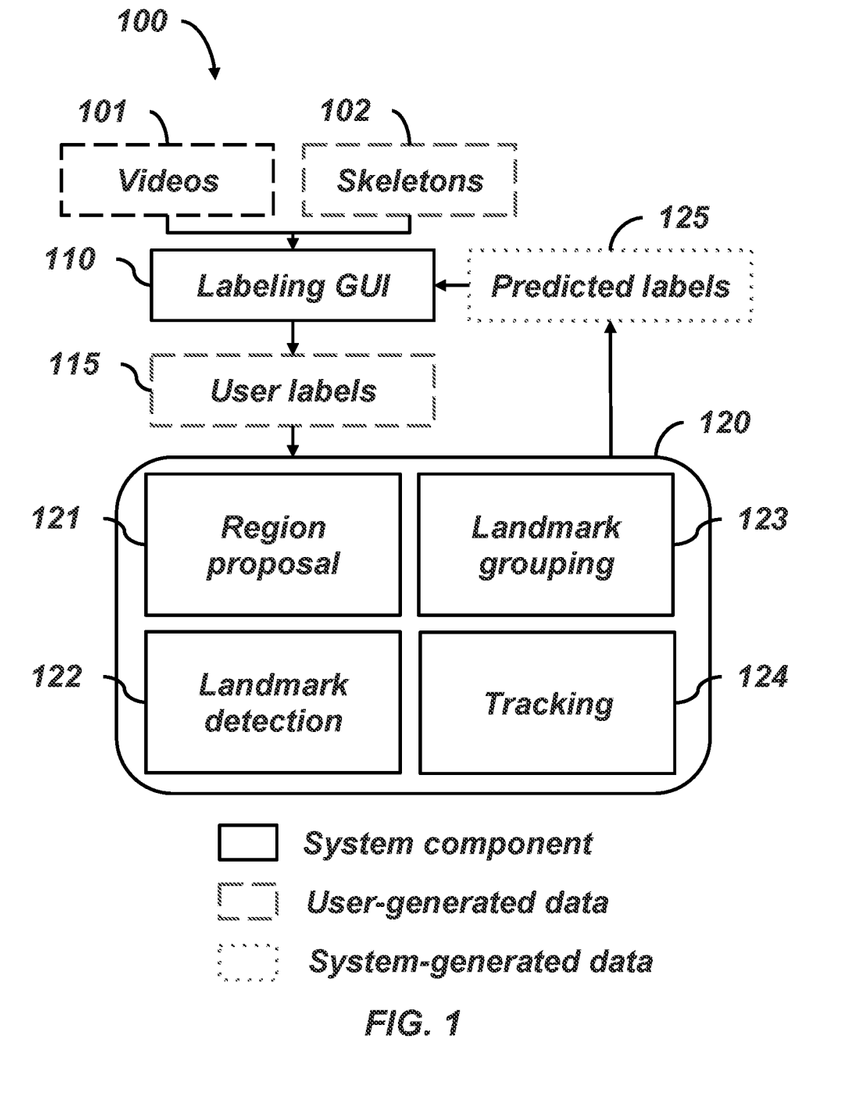
FIG. 1 is a flowchart illustrating the processing flow within an embodiment of a disclosed system.
Figure 2:
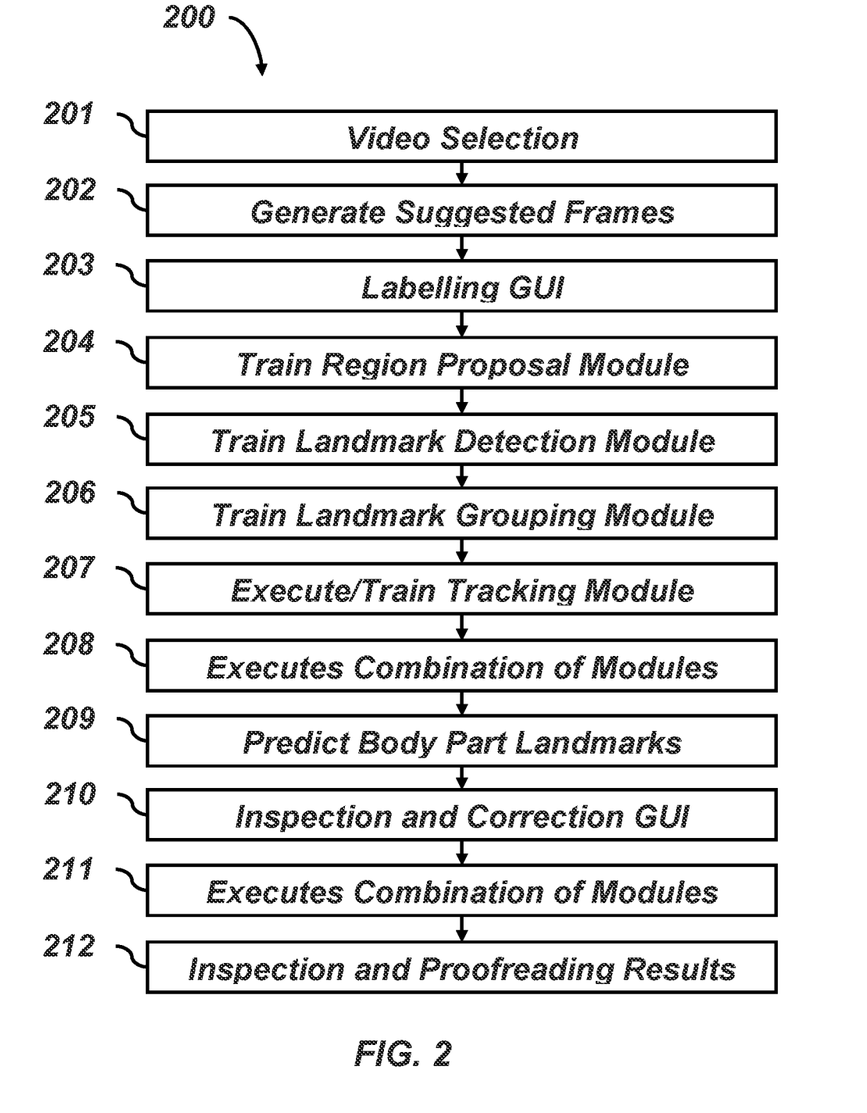
FIG. 2 is a flowchart of an embodiment of a method used by embodiments of the disclosed system.

Embodiments of the disclosed system can be seen in reference to FIGS. 1 and 2. Generally, the systems comprise at least one processor and at least one memory containing instructions that, when executed, cause the processor to perform certain functions, described below. The processor and memory may be associated with, e.g., a server, a desktop computer, or a virtual machine upon which various machine-readable instructions are causing the system to follow the disclosed technique. For example, one embodiment utilizes a high end consumer-grade workstation equipped with an Intel Core i7-5960X CPU, 128 GB DDR4 RAM, NVMe SSD drives, and a single NVIDIA GeForce 1080 GTX Ti (12 GB) GPU, while another used a high performance computing cluster with nodes equipped with NVIDIA P100 GPUs for batch processing.

In an embodiment of the disclosed system, videos of behaving animals are first recorded.

The system receives any number of videos (101) and, typically, at least one predetermined animal skeletons or animal skeletons designed by the user (102). As used herein, the term "skeleton" refers to a set of named landmarks on an animal and directed connections between them. In some embodiments, the user may select the videos containing animals behaving (201) to be used for a particular project via, e.g., a video selection GUI, which may be a GUI known to those of skill in the art that allows the user to select particular files saved to a hard drive, CD, DVD, USB flash drive, or other storage media known to those of skill in the art.

While the video recordings are generally understood as having sequential images of the same animal, the recordings may use different animals, including animals of the same species or genus, provided, e.g., that the movements of the body parts of different animals do not differ by a statistically significant margin. Similarly, while the video recordings are generally understood as occurring under constant imaging conditions (lighting, resolution, etc.), such is not required.

The system continues by generating a set of suggested frames (202) for labeling by extracting image features from random frames within the videos, grouping them according to similarity, and selecting a similarly sized subset from each group (this is meant to promote diversity in suggestions). In some embodiments, generating a set of suggested frames includes randomly sampling frames from the selected video recordings, summarizing the contents of these images, applying the k-means clustering algorithm to these summary descriptions, and then sampling a fixed maximum number of images from each cluster. Summarizing the contents of the images can include various optional techniques. Those techniques include: (1) flattening all image pixels, computing their principal components via eigen decomposition, and projecting each image onto a user-specified number of top principal components as defined by their variance; (2) detecting interest points using the Binary Robust Invariant Scalable Keypoints (BRISK) algorithm and computing the Histogram of Oriented Gradients (HOG) descriptors of the image region around each interest point; (3) detecting interest points using the BRISK algorithm and computing the BRISK descriptors of the image region around each interest point; or (4) detecting and summarizing interest points using the BRISK/HOG method or BRISK/BRISK method and computing the principal components of the set of image region descriptors.

The system continues through the use of one or more graphical user interface(s) (110, 203) that provide a variety of functions. While the figures show a single "Labeling GUI", it will be understood by those of skill in the art that this can include multiple user interfaces, depending on particular design choices.

First, the interface(s) allow a user to navigate to and view individual frames within the one or more selected video recordings.

Second, the interface(s) allow the user to specify a skeleton to be tracked. In some embodiments, the skeleton to be tracked comprises a set of named nodes representing identifiable landmarks on the body of the animal (e.g., joints, etc.), and a set of ordered pairs of named nodes representing the connections between the nodes.

Third, the interface(s) allow the user to label video frames by creating instances of the skeleton on top of the image and then positioning each landmark of each instance at their correct location within the images via draggable markers.

Figure 3:
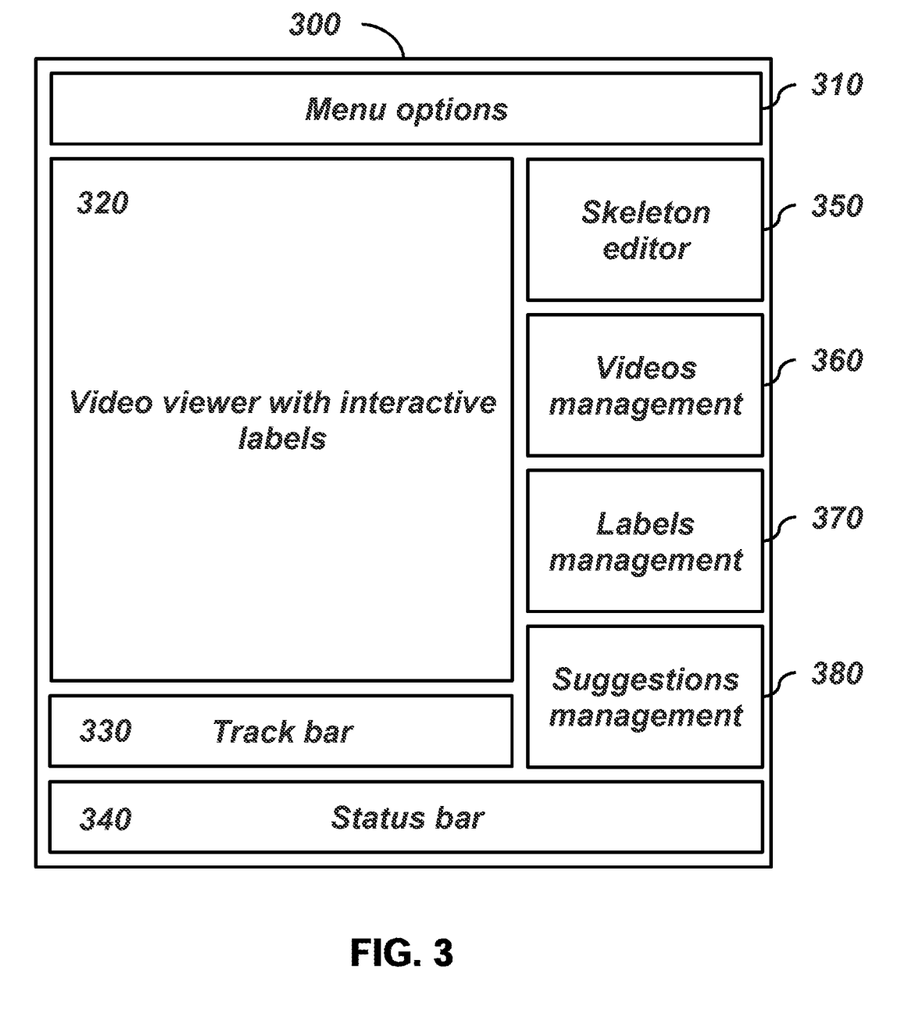
FIG. 3 is a block diagram illustrating an embodiment of a graphical user interface that can be used with the disclosed technique.

FIG. 3 provides an example of GUI (300) that can be used as, e.g., the main application GUI. As seen in FIG. 3, the GUI (300) may include a menu option bar or similar (310), The GUI (300) also includes a video viewer (320) with interactive labels. This is the primary window the user will be interacting with. The GUI may also include a track bar (330), and a status bar (340). The GUI may also include a portion for editing skeletons (350), managing videos (360) (including adding or removing videos from a given project), managing labels (370), and managing suggestions (380).

Figure 4:
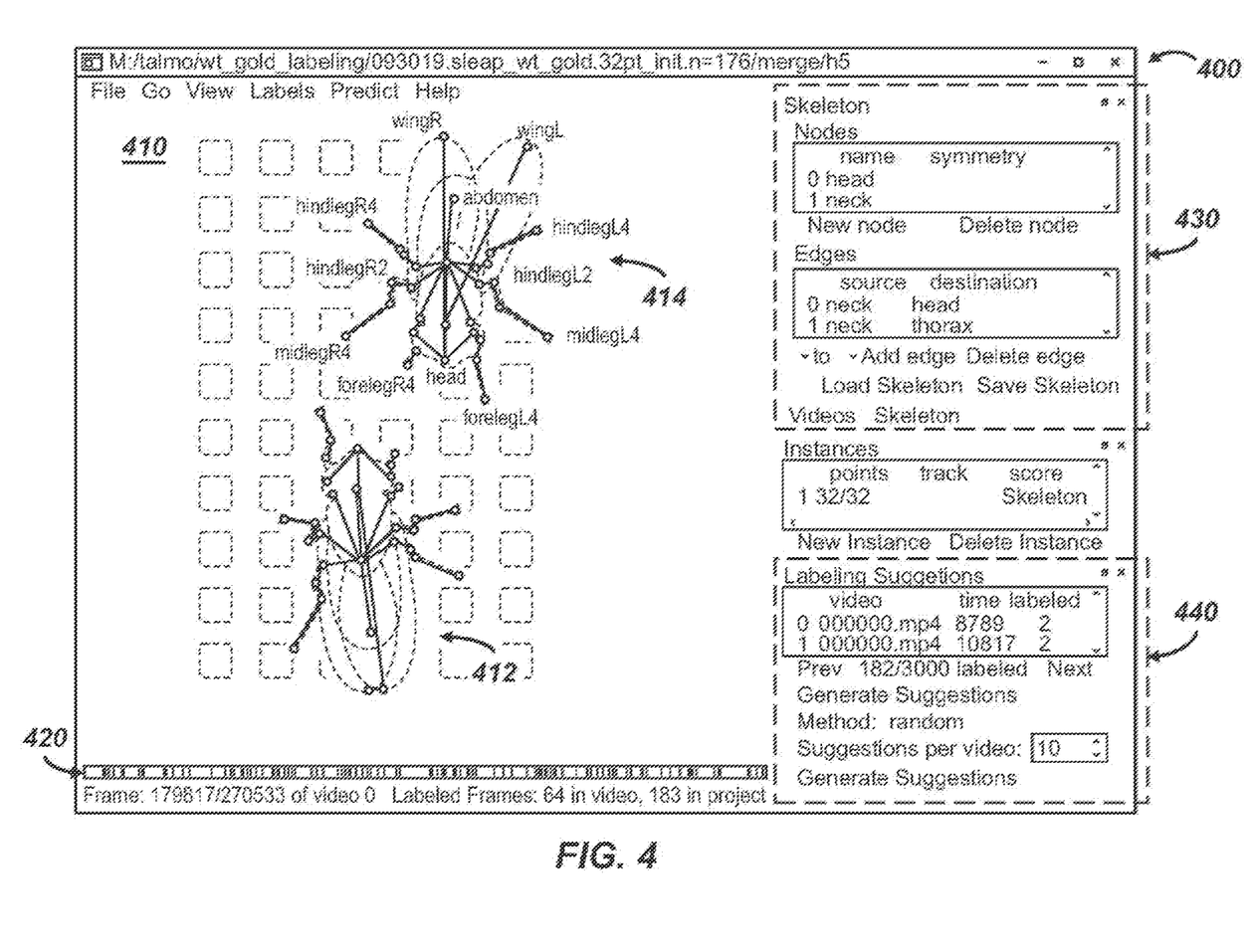
FIG. 4 is an image illustrating an embodiment of a graphical user interface that can be used with the disclosed technique.

FIG. 4 provides a specific embodiment of a GUI (400) which shows a large portion of the GUI displaying the current frame with labels (410). This particular example shows two animals displayed simultaneously, one that has been labelled by a user (413) and one that has only been estimated by a neural network (411). In some embodiments, the GUI may display labels in a color, such as yellow for labels that were "initialized" or estimated by a neural network (412), while it may display labels a second color, such as green for labels where a user has clicked and/or dragged the label to fix it (414). In some embodiments, the GUI may also display a descriptive name, such as "Head" or "wingR" or "highlegL4" near each user-corrected label. Below the current frame may be a portion showing progress indicators (420) display, for example, how many or what percentage of the frames have been initialized, and/or how many or what percentage of the frames have been labelled by the user. Adjacent to the current frame displayed (410) may be a portion with skeleton and video management (430). Adjacent to the current frame displayed (410) may also be a portion showing suggestions, such as suggested frames for labeling (440), including options to generate new suggestions.

Fourth, the interface(s) allow the user to select between pre-configured profiles for training neural network modules based on the labeled data. In some embodiments, the training profiles comprise a set of configuration options that define the module type, neural network backbone type, neural network architectural parameters, data preprocessing procedure, optimization procedure, data augmentation procedure, and configuration options pertaining to training the core modules of the system.

Once the user has interactively labelled frames or corrected from predicted labels generated by the system (described in further detail below), those user labels (115) are then sent to one or more inference modules (120).

Optionally, the system may train (204) a region proposal module (121) for detecting the center or extent of a region that the animal(s) occupy within an image. In some embodiments, the region proposal module comprises a configurable convolutional neural network and the training and inference procedures for predicting the center or extent that animal(s) occupy within images. In some embodiments, the inference procedures for the region proposal module comprise a set of machine readable instructions for proposing bounding boxes of fixed size around the detected centers, where the fixed size is calculated from sizes present in the labeled data or specified by the user, and merged when they significantly overlap.

The system trains (205) a landmark detection module (122) for detecting landmarks similar to the ones labeled by the user. In some embodiments, the landmark detection module comprises a configurable neural network and the training and inference procedures for predicting image coordinates of any number of instances of each landmark type. In some embodiments, the inference procedures for neural networks in the region proposal and landmark detection modules comprise a set of machine readable instructions to find a local maxima in each confidence map image, and refine the local maxima by upsampling a small area around each local maxima using bicubic interpolation and finding the global maximum within these confines whose relative location is used to offset the original coordinates of each local maxima. In some embodiments, one or more neural networks in the landmark detection module are trained to predict, from unmarked images of an animal, for each landmark type, a representation of the location of body landmarks where each pixel corresponds to the probability of the body landmark being present at a given location.

The system may optionally train (206) a landmark grouping module (123) for grouping detected landmarks based on the connections specified in the skeleton. In some embodiments, the landmark grouping module comprises a configurable neural network and the training and inference procedures for predicting the connections between detected landmarks. In some embodiments, neural networks in the landmark grouping module are trained to predict, from unmarked images of the animal, for each connection between landmark types, a representation of the relative spatial offset between the two body part landmarks that form the connection (part affinity fields) where each pixel corresponds to the unit vector that is oriented from the source landmark to the destination landmark. In some embodiments, the inference procedures for neural networks in the landmark grouping module comprises a set of machine readable instructions to group pairs of landmark types optimally by evaluating the similarity of the orientation derived from the line formed by the pair of landmarks, and the orientation derived by taking the average of the unit vectors along the same line on the predicted relative spatial offset between the two body part landmarks that form the connection (predicted part affinity fields).

The system may optionally execute or train (207) a tracking module (124) for grouping detections of the same animals across frames. In some embodiments, the tracking module comprises a set of machine-readable instructions to perform optimal matching between detected instances in different frames, by using image features as similarity or pairwise affinities learned through a configurable neural network and the training and inference procedures to produce them. In some embodiments, the optimal matching in the tracking module comprises a set of machine readable instructions to associate detected instances across consecutive frames by greedy assignment of maximum similarity of instances based on underlying image features or learned affinities, or by applying predicted displacements of each landmark derived from optical flow calculation and then using the similarity of the resulting body configuration to rank assignments.

The system continues by executing a combination (208) of the region proposal module (121), landmark detection module (122), landmark grouping module (123), and/or tracking module (124) to predict the extent of animals, locations of body landmarks, and/or connections between detected body landmarks on any new images of the same animals or those similar in appearance (as discussed previously).

The system continues by predicting body part landmarks (209) of animals within unlabeled images. In some embodiments, this also includes grouping body part landmarks of animals within the unlabeled images.

The system continues by displaying one or more graphical user interface(s) (here, shown as the same labeling GUI (110)) for inspection and correction (210) of the results/automatically predicted labels (125) for further training, which may be, e.g., prioritized by prediction score.

The system continues by executing all modules configured or trained by the user on additional video recordings of the same or similar animals (211), and then displaying one or more graphical user interfaces (212) for inspection and proofreading of the results. This GUI may be the same labeling GUI (110) or may be a separate GUI.

On images with multiple animals, the system uses a body part grouping module to associate multiple body part detections to the correct individuals. The system groups body parts by training neural networks to predict part affinity fields (PAFs), directional vector fields along the animal skeleton within the image coordinates. As known to those of skill in the art, a PAF is a set of flow fields that encodes unstructured pairwise relationships between body parts. Body part detections are grouped by iteratively adding candidate body part detections that have similar directional vector fields to the relative position of each candidate. Grouped sets of body part detections belonging to the same animal are referred to as "instances". The system is generalizable to any skeleton that forms a tree structure. The system is modular with regard to the neural network architecture that generates the part affinity fields.

On videos (sequences of images) of multiple animals, the system links instances across frames. The system computes measures of similarity between candidate instances across frames and performs global matching of candidates via a simple linear program (Munkres algorithm). The system is modular to the similarity measure, which includes distances in time and space, similarity of identity tags derived from image features, learned pairwise measures, or similarity to predicted displacements. When the similarity measure is selected to be similarity to predicted displacements, this module may, e.g., implement the FlowTrack algorithm (available at arxiv.org/abs/1804.06208) with the Farneback optical flow algorithm (published at link.springer.com/chapter/10.1007/3-540-45103-X_50).

A simplified embodiment of the disclosed technique can be seen in regard to the following example.

After receiving a set of images that comprised a 30 minute video of a pair of male and female fruit flies (*Drosophila melanogaster*) interacting in a 30 mm diameter circular arena covered by a clear dome and imaged under infrared illumination at a resolution of 1024×1024 pixels (30.3 pixel/mm) at 150 frames per second.

A skeleton was defined as a set of 32 different landmark types (nodes) representing anatomically distinct points along the body of fruit flies. Additionally, 31 connections between landmark types (edges) were defined such that they formed a directed acyclic graph with a path from the root node (thorax) to every other node.

Suggestions for which frames to label were generated by randomly sampling 1000 frames from the video, computing BRISK interest points in these images, extracting a descriptor of the visual appearance around these points also using BRISK, applying principal components analysis to the descriptors, projecting of the visual appearance descriptors onto the first 50 principal components, and finally clustering on these vectors with k-means with 10 clusters and sampling 100 frames from each cluster.

Labeling was done interactively by manually placing the landmarks of each instance (one per animal) onto their correct coordinates in image space. This was done for both animals present in 10 of the suggested frames.

The region proposal module was trained in order to estimate the region occupied by each animal within the frame. Centroids were computed by finding the median of the labeled coordinates for each instance in each frame. Confidence maps were generated by producing images representing an unnormalized 2D Gaussian distribution centered at each coordinate with a standard deviation of 5. The network was trained to receive full frames at a 0.25× resolution (256×256×1) and output single channel confidence maps (sigma=5) of the centroid at the same resolution.

Images and associated centroids were augmented by applying random rotations from the range −180° to 180°. 10% of the input data was reserved as a validation set and the rest assigned to the training set. The backbone selected was a UNet with: 3 blocks of 2 convolutions with 5×5 kernels with a starting number of filters of 16, doubled at every block, ReLU activation function, followed by a 2D max pooling operation with a 2×2 receptive field with a stride of 2 to reduce the width and height of the feature maps at every block; 3 blocks with a symmetric architecture and skip connections from the pooling blocks, with a bilinear upsampling layer with a factor 2 before the convolutions and no pooling; and a final convolutional layer with linear activation and the same number of channels as the confidence maps. The optimization was performed by updating the weights using the Adam optimizer with AMSgrad enabled and an initial learning rate of 0.0001 against a mean squared error loss. A single step consisted of a batch of 2 augmented images, and training was done for 200 steps per epoch for a maximum of 100 epochs. At the end of every epoch, the loss was evaluated on the validation set and learning rate was reduced by a factor of 0.5 if it had not improved for 5 epochs. Training was terminated early if the validation loss did not improve by more than 1e−8 for 15 epochs. After training, predicted confidence maps could be converted back into coordinates by finding local peaks via non-maximum suppression.

The landmark detection module was trained in order to estimate the coordinates of each body part within the occupied regions. 32 landmark types were annotated per instance, generating a confidence map for each part type, ignoring landmarks labeled as not visible. Confidence maps were generated by producing images representing an unnormalized 2D Gaussian distribution centered at each coordinate with a standard deviation of 5. The network was trained to receive cropped regions of frames at full resolution, with the cropping informed by the ground truth coordinates used to compute centroids, around which a bounding box of size (256×256×1) was cropped, and output multi-channel confidence maps. An additional 10 random crops of the background were produced such that they did not overlap with the instance bounding boxes and trained to output confidence maps with no detections. Images and associated coordinates were augmented by applying random rotations from the range −180° to 180°. 10% of the input data was reserved as a validation set and the rest assigned to the training set. The backbone selected was a UNet with: 3 blocks of 2 convolutions with 5×5 kernels with a starting number of filters of 64, doubled at every block, ReLU activation function, followed by a 2D max pooling operation with a 2×2 receptive field with a stride of 2 to reduce the width and height of the feature maps at every block; 3 blocks with a symmetric architecture and skip connections from the pooling blocks, with a bilinear upsampling layer with a factor 2 before the convolutions and no pooling; and a final convolutional layer with linear activation and the same number of channels as the confidence maps. The optimization was performed by updating the weights using the Adam optimizer with AMSgrad enabled and an initial learning rate of 0.0001 against a mean squared error loss. A single step consisted of a batch of 2 augmented images, and training was done for 200 steps per epoch for a maximum of 100 epochs. At the end of every epoch, the loss was evaluated on the validation set and learning rate was reduced by a factor of 0.5 if it had not improved for 5 epochs. Training was terminated early if the validation loss did not improve by more than 1e−8 for 15 epochs. After training, predicted confidence maps could be converted back into coordinates by finding local peaks via non-maximum suppression.

The landmark grouping module was trained in order to group detections of each body part within the occupied regions within each instance. 31 edges (connections) between body parts were defined in the skeleton, generating a part affinity field for each part type, ignoring landmarks labeled as not visible. Part affinity fields were generated by producing images representing the spatial direction to move from each source landmark coordinate to each destination landmark coordinate. Fields were defined up to 5 pixels away from the line connecting landmarks. The x- and y-components of the field at each pixel were stored as separate image channels and concatenated channel-wise for all connections. The network was trained to receive cropped regions of frames at full resolution, with the cropping informed by the ground truth coordinates used to compute centroids, around which a bounding box of size (256×256×1) was cropped, and output multi-channel part affinity fields at half resolution (128×128×62). An additional 10 random crops of the background were produced such that they did not overlap with the instance bounding boxes and trained to output part affinity fields with no connections. Images and associated coordinates were augmented by applying random rotations from the range −180° to 180°. 10% of the input data was reserved as a validation set and the rest assigned to the training set. The backbone selected was a LEAP CNN with: 3 blocks of 2 convolutions with 3×3 kernels with a starting number of filters of 32, doubled at every block, ReLU activation function, followed by a 2D max pooling operation with a 2×2 receptive field with a stride of 2 to reduce the width and height of the feature maps at every block; 2 blocks with a symmetric architecture, with a bilinear upsampling layer with a factor 2 before the convolutions and no pooling; and a final convolutional layer with linear activation and the same number of channels as the part affinity fields. The optimization was performed by updating the weights using the Adam optimizer with AMSgrad enabled and an initial learning rate of 0.00005 against a mean squared error loss. A single step consisted of a batch of 2 augmented images, and training was done for 200 steps per epoch for a maximum of 100 epochs. At the end of every epoch, the loss was evaluated on the validation set and learning rate was reduced by a factor of 0.5 if it had not improved for 5 epochs. Training was terminated early if the validation loss did not improve by more than 1e−8 for 15 epochs. After training, predicted part affinity fields were used to group detected coordinates by scoring each pair of associations by the cosine similarity between the average of part affinity field vectors along the line segment formed by the pair of candidate landmark coordinates, and the line segment itself. Instances were constructed by greedy association of highest scoring associations for each connection type.

After training these modules, the region proposal, landmark detection, and landmark grouping were executed on remaining suggested frames in order to generate predicted labels. Predicted labels were corrected until 100 frames had confirmed labels. Then, the modules were trained again with the same configuration specified previously, but with the larger set of labeled data.

Once modules were retrained, these were executed as previously but on all frames of the video instead of only on suggested frames. Additionally, the tracking module was executed such that the detected instances were associated over time. Tracking was performed by applying the Farneback optical flow algorithm at the locations of the predicted landmark coordinates, and the computed displacements applied such that predicted instances from previous frames were mapped onto the current frame. Then, instances detected in the current were associated with shifted instances by their similarity derived from the pairwise distances between coordinates of matching body parts. Shifted instances were considered for a window of up to 30 frames prior.

What is claimed:

1. An automated system for measuring and predicting animal body part dynamics comprising:
   a processor and memory containing machine readable instructions that, when executed:
   a. displays one or more graphical user interfaces that allow a user to select one or more video recordings of one or more animals behaving;
   b. generates a set of suggested frames for labeling by extracting image features from random frames within the one or more video recordings, groups the random frames according to similarity, and selects a similarly sized subset from each group;
   c. displays one or more graphical user interfaces that allow a user to navigate to and view individual frames within the selected one or more video recordings, to specify a skeleton to be tracked, to label a plurality of landmarks in at least one of the suggested frames by creating instances of the skeleton on top of each of the at least one of the suggested frames and then positioning each landmark at a correct location within the at least one of the suggested frames via draggable markers, and to select between pre-configured profiles for training neural network modules based on the labeled data;
   d. optionally trains a region proposal module for detecting a center or extent of a region that the one or more animals occupy within an image;
   e. trains a landmark detection module for detecting landmarks similar to the ones labeled by the user;
   f. optionally trains a landmark grouping module for grouping detected landmarks based on the connections specified in the skeleton;
   g. optionally executes or trains a tracking module for grouping detections of the same animals across frames;
   h. executes a combination of the region proposal module, landmark detection module, landmark grouping module, and tracking module to predict the extent of animals, locations of body landmarks, and connections between detected body landmarks, on any new frames of the same animals or those similar in appearance;
   i. predicts and optionally groups body part landmarks of animals within unlabeled frames;
   j. displays a graphical user interface for inspection and correction of predicted landmarks for further training, optionally prioritized by prediction score;
   k. executes all modules configured or trained by the user on any new video recordings of the same or similar animals; and
   l. displays a graphical user interface for inspection and proofreading of predicted landmarks.

2. The automated system according to claim 1, wherein the video recordings of animals behaving comprise sequential images of animals of any species.

3. The automated system according to claim 1, wherein the skeleton to be tracked comprises a set of named nodes representing identifiable landmarks on the body of the animal, and a set of ordered pairs of named nodes representing the connections between the nodes.

4. The automated system according to claim 1, wherein the instructions for generating suggested frames for labeling comprises a set of machine readable instructions for randomly sampling frames from the selected one or more video recordings, generating summary descriptions by summarizing the contents of these randomly sampled frames, applying a k-means clustering algorithm to these summary descriptions, and then sampling a fixed maximum number of frames from each cluster, wherein summarizing each randomly sampled frame includes:
   m. flattening all pixels of the frame, computing their principal components via eigen decomposition, and projecting each frame onto a user-specified number of top principal components as defined by variance of the principal components;
   n. detecting interest points using the Binary Robust Invariant Scalable Keypoints (BRISK) algorithm and computing the Histogram of Oriented Gradients (HOG) descriptors of the frame region around each interest point;
   o. detecting interest points using the BRISK algorithm and computing the BRISK descriptors of the frame region around each interest point; or
   p. detecting and summarizing interest points using any of the methods (n)-(o), and computing the principal components of the HOG or BRISK descriptors of the frame region around each interest point.

5. The automated system according to claim 1, wherein the training profiles comprise a set of configuration options that define the module type, neural network backbone type, neural network architectural parameters, data preprocessing procedure, optimization procedure, data augmentation procedure, and configuration options pertaining to training the core modules of the system.

6. The automated system according to claim 1, wherein the region proposal module comprises a configurable convolutional neural network and the training and inference procedures for predicting the center or extent that animal(s) occupy within frames.

7. The automated system according to claim 1, wherein the landmark detection module comprises a configurable neural network and the training and inference procedures for predicting frame coordinates of any number of instances of each landmark type.

8. The automated system according to claim 1, wherein neural networks in the landmark detection module are trained to predict, from unmarked frames of the animal, for each landmark type, a representation of the location of body landmarks where each pixel corresponds to the probability of the body landmark being present at a given location.

9. The automated system according to claim 1, wherein the inference procedures for neural networks in the region proposal and landmark detection modules comprise a set of machine readable instructions to find a local maxima in each confidence map image, and refine the local maxima by upsampling a small area around each local maxima using bicubic interpolation and finding the global maximum within the small area around each local maxima whose relative location is used to offset the original coordinates of each local maxima.

10. The automated system according to claim 1, wherein the inference procedures for the region proposal module comprise a set of machine readable instructions for proposing bounding boxes of fixed size around the detected centers, where the fixed size is calculated from sizes present in the labeled data or specified by the user, and merged when the bounding boxes significantly overlap.

11. The automated system according to claim 1, wherein the landmark grouping module comprises a configurable neural network and the training and inference procedures for predicting the connections between detected landmarks.

12. The automated system according to claim 1, wherein neural networks in the landmark grouping module are trained to predict, from unmarked frames of the animal, for each connection between landmark types, a representation of the relative spatial offset between the two body part landmarks that form the connection where each pixel corresponds to the unit vector that is oriented from the source landmark to the destination landmark.

13. The automated system according to claim 1, wherein the inference procedures for neural networks in the landmark grouping module comprises a set of machine readable instructions to group pairs of landmark types optimally by evaluating the similarity of the orientation derived from the line formed by the pair of landmarks, and the orientation derived by taking the average of the unit vectors along the same line on the predicted part affinity fields.

14. The automated system according to claim 1, wherein the tracking module comprises a set of machine readable instructions to perform optimal matching between detected instances in different frames, by using frame features as similarity or pairwise affinities learned through a configurable neural network.

15. The automated system according to claim 14, wherein the optimal matching in the tracking module comprises a set of machine readable instructions to associate detected instances across consecutive frames by greedy assignment of maximum similarity of instances based on underlying frame features or learned affinities, or by applying predicted displacements of each landmark derived from optical flow calculation and then using the similarity of the resulting body configuration to rank assignments.

16. The automated system according to claim 1, wherein the system comprises at least one module having a configurable neural network with a layered network architecture comprising:
  a configurable backbone (early neural network layers) having a compatible convolutional neural network architecture; and
  a configurable head (final output neural network layers) having compatible neural network layers whose output resembles the output of the at least one module.

17. The automated system according to claim 1, wherein the system comprises a backbone with an architecture selected from the group consisting of LEAP CNN, UNet, Stacked Hourglass, DenseNet, ResNet optionally initialized with pretrained weights, HRNet, or a user-specified convolutional neural network architecture.

18. The automated system according to claim 1, wherein the system comprises a backbone, and wherein configuration options of the backbone comprise the set of parameters that specify the variant of the backbone architecture to use, specifically:
  i. number of convolutional filters;
  ii. size of convolutional filters;
  iii. layers per block;
  iv. number of blocks with pooling (frame feature scale reduction);
  v. number of blocks with upsampling (frame feature scale increase);
  vi. number of stacks (copies of the backbone); and
  vii. any parameter specific to a given backbone.

19. The automated system according to claim 1, wherein the system specifies:
  i. data preprocessing procedure;
  ii. data augmentation procedure;
  iii. optimizer algorithm;
  iv. learning rate schedule;
  v. checkpointing procedure; and
  vi. duration of the training procedure.

20. The automated system according to claim 1, wherein the execution procedures for the combination of modules comprises a set of machine readable instructions to execute the functionality provided by each module in a specified sequence, specifically:
  executing the landmark detection module to detect peaks in full sized frames without grouping;
  executing the region proposal module to crop the image around each animal, then executing the landmark detection module to detect peaks in cropped frames without grouping;
  executing the landmark detection module to detect peaks in full sized frames, then executing the landmark grouping module to group the detected peaks in the full sized frames; or
  executing the region proposal module to crop the frame around each animal, executing the landmark detection module to detect peaks in cropped frames, then executing the landmark grouping module to group the detected peaks in the cropped frames.

21. The automated system according to claim 1, further comprising executing the tracking module to group peaks over consecutive frames.

* * * * *